United States Patent [19]

Schoengen et al.

[11] 4,269,805
[45] May 26, 1981

[54] REACTOR FOR THE OXIDATION OF ALKYL AROMATICS WITH OXYGEN-CONTAINING GASES IN THE LIQUID PHASE

[75] Inventors: Anton Schoengen, Witten; Heinrich Schroeder, Dortmund-Syburg, both of Fed. Rep. of Germany

[73] Assignee: Dynamit Nobel Aktiengesellschaft, Troisdorf, Fed. Rep. of Germany

[21] Appl. No.: 11,656

[22] Filed: Feb. 12, 1979

[30] Foreign Application Priority Data

Feb. 13, 1978 [DE] Fed. Rep. of Germany ....... 2805915

[51] Int. Cl.$^3$ ............................. B01J 8/10; B01J 8/12; C07C 51/21; G05D 9/00
[52] U.S. Cl. .................................... 422/106; 422/190; 422/191; 422/194; 422/200; 422/215; 422/226; 422/231; 422/229; 422/235
[58] Field of Search ............... 422/106, 110, 111, 193, 422/194, 195, 200, 208, 225, 226, 228, 231, 234, 235, 236; 562/413, 414, 412 VS

[56] References Cited

U.S. PATENT DOCUMENTS

| | | | |
|---|---|---|---|
| 2,760,850 | 8/1956 | Lambert et al. | 422/194 |
| 2,920,124 | 1/1960 | Stiles et al. | 422/225 X |
| 3,065,061 | 11/1962 | Fett | 422/200 |
| 3,199,959 | 8/1965 | Dempsey | 422/193 |
| 3,271,433 | 9/1966 | Bentz | 422/193 X |
| 3,845,117 | 10/1974 | Kollar | 562/413 |
| 3,883,309 | 5/1975 | Ishizawa et al. | 422/106 |

Primary Examiner—Bradley Garris
Attorney, Agent, or Firm—Craig and Antonerlli

[57] ABSTRACT

A multi-stage reactor for the oxidation of alkyl aromatics, e.g. a mixture of p-xylene and methyl p-toluate in a liquid phase reaction mixture with oxygen-containing gases, e.g. air, under elevated pressure and at an elevated temperature in the presence of an oxidation catalyst is in the form of an elongated closed tank with a multiplicity of neighboring reaction chambers arranged successively from one end to the other end of the tank for containing the liquid reaction mixture at predetermined levels in each chamber. The reactor is provided with an oxidizing gas feed system for introducing an oxidizing gas into each chamber, feed means for introducing at least one alkyl aromatic reactant and an oxidation catalyst into at least one of the reaction chambers, a vapor-collecting conduit means in communication with each of said chambers for removing reaction gas from each of said chambers, and a discharge means for removing the oxidized product from the reactor tank. An internally disposed cooling conduit system containing a coolant for removing the heat of reaction is provided and includes a group of cooling conduits for each of the reaction chambers. These groups have horizontally disposed cooling conduits through which a cooling medium flows.

27 Claims, 13 Drawing Figures

REACTOR FOR THE OXIDATION OF ALKYL AROMATICS WITH OXYGEN-CONTAINING GASES IN THE LIQUID PHASE

The invention relates to a reactor for the oxidation of alkyl aromatics, especially mixtures of p-xylene (p-X) and methyl p-toluate (pTE) in the liquid phase with oxygen-containing gases under elevated pressure and at an elevated temperature in the presence of an oxidation catalyst. This oxidation reaction is known worldwide as being part of the "Written" or "Katzschmann" process for the production of dimethyl terephthalate and is described in many patents and literature references, e.g. German Pat. Nos. 949,564; 1,041,945; 2,010,137 and U.S. Pat. No. 2,894,978. More particularly, this invention relates to a reactor for effecting this known oxidation process which has a multi-compartment tank with an oxidizing gas feed system, feed means for p-xylene, catalyst, and methyl p-toluate, a vapor conduit on the outside of the tank, a discharge system for the oxidized product, and internally horizontally disposed cooling pipe systems containing a coolant for removing the heat of reaction from each of the compartments.

The oxidation reactors of the prior art type are vertically disposed, cylindrical containers having a height of about 18-30 meters with vertically installed cooling pipes, exposed to longitudinal flow, to remove the heat of reaction by means of a cooling medium (U.S. Pat. No. 3,065,061 and German Patent Application No. P 22 50 431). For other processes intended for the oxidation of p-X to terephthalic acid, stirred-tank cascades without pipe installations are conventional. In these devices, cooling is effected by directly evaporating solvent.

The oxidation of mixtures of p-X and pTE takes place in one stage or in several series-connected stages, wherein in each stage the oxidizing gas flows through the entire reaction chamber from the bottom toward the top. In this connection, two or more superimposed air feed inlet lines for the oxidation gas in an oxidizer stage are likewise known, wherein an oxidation reactor is utilized for each stage, and the reaction product passes through the stages continuously. A maximally large number of reaction stages is desirable, because optimum reaction conditions can thereby be obtained.

It is likewise known that the reaction takes place more gradually in the latter stages than in the initial stages. As a consequence thereof, with the use of oxygen-containing gases and/or air as the oxidizing gas, the oxygen consumption while passing through the last stage is lower than during passage through the first stage. To compensate for this effect, starting material is also added in the latter stages under practical conditions.

On account of the structural height of the oxidation reactors, a high liquid column is formed which must be traversed by the oxidizing gas. In this process, a pressure differential occurs between the surface of the liquid and the air introduction system at the bottom of the oxidation reactors; this pressure differential must be overcome by compressors in addition to the operating pressure.

The height of the known oxidation reactors is extensively determined by the construction of the cooling surfaces. The necessary large cooling surfaces are obtained by extending long, vertical pipes, bent at an angle at the top and at the bottom, through the sidewalls of the oxidation reactor. These cooling pipes terminate in externally welded-on vapor or condensate chambers. Since the number of bores in the walls of the oxidation reactor is limited for reasons of strength of material of the wall, the number of cooling pipes is likewise limited. If it were desired to design such oxidation reactors for higher outputs, then there would merely be the possiblity to lengthen the cooling pipes in order to increase the cooling surface. With increasing plant outputs, this resulted in the heretofore mentioned large heights of the oxidation reactors and/or caused the diameters of the oxidation reactors to become so large that difficulties were encountered during the transportation from the factory to the installation site of the oxidation reactors.

Another construction is conventional wherein the vertical cooling pipes in the reactor are combined at a collector in the head of the reactor. This arrangement leads to very large structural heights in case of higher plant outputs.

If the oxidation is conducted in several stages, it is necessary in the oxidation reactors known at the present time to include for each single stage a set of measuring and regulating units, connecting pipelines, safety means, foundations, etc. This leads to the tendency to provide a relatively small number of stages, for reasons of expenses.

The cooling pipes exposed to a longitudinal flow in oxidation reactors according to the prior art exhibit a relatively poor heat transfer characteristic. Thus, in the construction known nowadays, one is forced to build relatively high oxidation reactors due to the required cooling surfaces. As a consequence, the volumes are poorly utilized, and the space-time yields are low.

The amounts of air fed at the relatively small diameters of the oxidation reactors lead to a foamy consistency of the contents of the reactor and easily result in overfoaming.

The high cover over the bubble plate used in such reactors leads to an enlargement in the amount of already consumed oxidizing gas still present in the liquid.

The inlet for the oxidizing gas is fashioned so that the oxidation reactor is fed from the bottom, and the oxygen is consumed along its path through the oxidation reactor in the upward direction. Before a reaction can take place, the oxidizing gas must be heated within the oxidation reactor. In the present construction, there are no agitator units installed, because very long shafts are required, resulting in high initial investment costs and technical difficulties. The reaction product must remain for an unnecessarily long period of time under the temperatures required for the oxidation, on account of the large structural heights of the oxidation reactors. This leads to decomposition reactions and thus to reductions in yield.

In the conventional oxidation reactors, almost the entire top half of the reaction chamber must be provided for the sole reason of accommodating the long cooling pipes that provide the cooling surfaces necessary to remove the heat of reaction. A large portion of the cooling surfaces is very far remote from the point of air introduction. As a consequence, the path of heat transport from the points where the heat of reaction is produced to the points where it is removed is very long. As a result, there are local hot spots which lead to losses in the yield of desired product.

Experimental measurements yielded the result that, with the use of air as the oxidizing gas for mixtures of p-xylene and methyl p-toluate, the oxygen was, depending on the particular stage, either completely consumed or at least consumed to such an extent that the oxygen concentrations in the waste gas were far below the explosive limits, already after traversing a column of the reaction mixture having a height of 3 meters or less.

Furthermore, calculations regarding the heat transfer characteristic showed that the heat tranfer values to be obtained at the existing conditions according to the above-described state of the art could be substantially improved by a different arrangement of the cooling pipes. It is known that, during the oxidation of mixtures of p-xylene and methyl p-toluate in the liquid phase and in the presence of oxidation catalysts which contain a heavy metal of cobalt or manganese and mixture of these metals, deposits of solids, e.g. terephthalic acid, can occur on the oxidation reactor walls and especially on the cooling pipes. However, in the past few years, it was possible to improve the conductance of the process and to improve the surface quality of the cooling pipes to such an extent that little or no deposits of solids were observed any more even on horizontally or obliquely installed portions of the cooling pipes. However, these improvements resulted in increased investment costs.

It is an object of the invention to avoid the above disadvantages of the conventional devices, such as high pressure losses, a long heat transport path, and a poor heat transfer. It is furthermore an object of this invention to increase the space-time yields attained by the reactor constructions known heretofore, to lower the initial investment costs, to reduce the space occupied by the system, to decrease energy costs, and to diminish the danger of overfoaming. Moreover, it is now possible to increase the number of stages in the oxidation reactors of this invention from the previous ratio, i.e. one stage per oxidation reactor, to a ratio of two or more stages per oxidation reactor.

With the aid of the reactors of this invention, the problem on which this invention is based is solved by providing that a reactor container or reactor tank has several preferably adjacent or superjacent reaction chambers or compartments successively traversed by the reaction mixture, that all reaction chambers are individually provided with bundles of horizontally installed cooling pipes, exposed to a transverse flow to serve as the cooling pipe systems, and with means for introducing the oxidizing gas; and that at least a portion of the reaction chambers includes feed means for p-xylene, catalyst, and methyl p-toluate, vapor outlet conduits, and outlet means for effecting discharge of the oxidized product from the reactor.

A person skilled in the art will see from the particularly advantageous embodiments described hereinbelow that there is a great variety of desirable features and advantages provided by the apparatus of this invention during the catalytic oxidation of mixtures of p-xylene and methyl p-toluate in the liquid phase with oxygen-containing gases under elevated pressure and at an elevated temperature; and that these features have not been realizable at all or to the same extent heretofore in the conventional apparatus.

It will be appreciated that the reactor of this invention is particularly suitable for effecting an improved multi-stage process, wherein a mixture of p-xylene and methyl p-toluate is partially oxidized in the first stage with a molecular oxygen-containing gas in a liquid phase, and in the second and subsequent stages additional oxidation is effected continuously with the further supply of p-xylene. The resulting product of the oxidation is then esterified with methanol in a separate reactor and the resulting dimethyl terephthalate is recovered. Each of the stages of this process are effected in a separate chamber or compartment of the reactor with the oxidation reaction becoming more complete in each successive stage as evidenced by the increased acid number of the contents of each chamber.

Moreover, it is possible by means of the apparatus of this invention to conduct the catalytic oxidation of other alkyl aromatics in the liquid phase with oxygen-containing gases under elevated pressure and at an elevated temperature, for example m-xylene and its intermediate oxidation products to isophthalic acid, toluene to benzoic acid, p-xylene or p-toluic aldehyde to terephthalic acid, and the like.

Thus, this invention contemplates a reactor unit for effecting oxidation of alkyl aromatics in a liquid phase reaction medium, which comprises an elongated tank or vessel, preferably a horizontal cylindrical tank, having separating baffle wall means arranged therein for providing a plurality of successively-arranged liquid-containing chambers or compartments within said tank, means for feeding at least one alkyl aromatic reactant into at least the first chamber of the successively-arranged chambers, oxidizing gas feed means for introducing a molecular oxygen-containing gas into each of said chambers below the liquid level therein, horizontally disposed cooling conduit means for removing the heat of reaction from said liquid phase reaction medium, said cooling means being arranged within each of the liquid-containing chambers so that the oxygen-containing gas introduced into the chamber passes over the cooling means before exiting from the liquid phase, liquid level control means for maintaining the liquid level in each of said chambers at a predetermined level and discharge means for removing the reaction products from the reactor.

A particularly advantageous embodiment of the invention consists in a horizontally disposed, cylindrical container wherein the reaction chambers, located in side-by-side relationship, are separated from one another by means of bulkheads or separating baffles and are provided with a system of interconnected vapor conduits.

Of course, such a cylindrical container can also be set up in an inclined position.

It will be appreciated that in accordance with this invention there are various embodiments of the reactor construction; in one embodiment, which is preferred, the reactor tank is positioned horizontally with the liquid-containing chamber arranged side-by-side; whereas in another embodiment, the reactor tank is positioned vertically and these liquid-containing chambers are arranged one above the other.

Figure 1A:
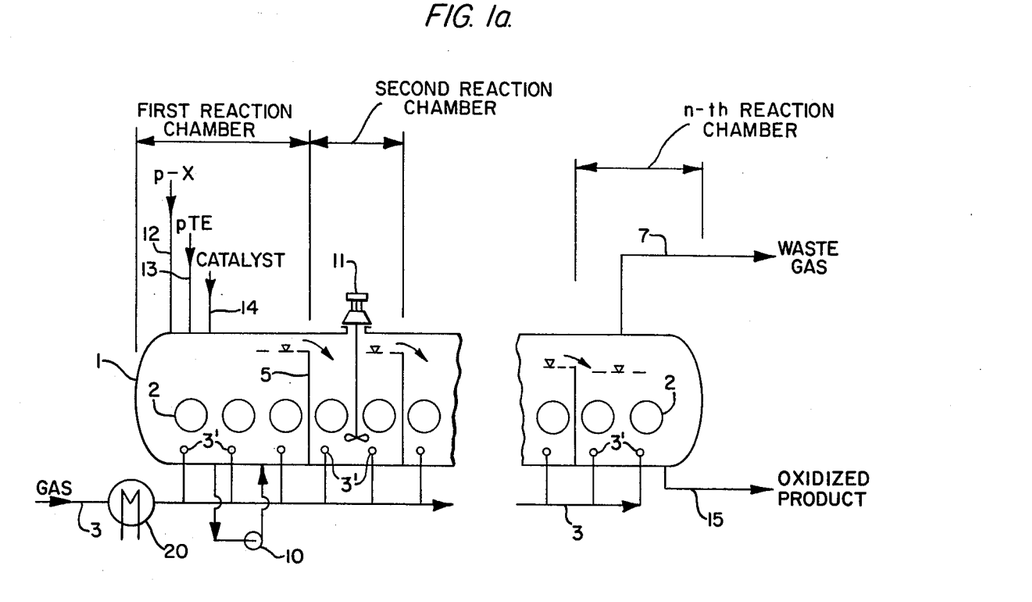
FIGS. 1a and 2 show horizontally disposed oxidation reactors with side-by-side reaction chambers subdivided by bulkheads or separating baffles and with auxiliary equipment, (a portion of each reactor has been removed to indicate that a number of additional chambers may be present in each embodiment)
Figure 1B:
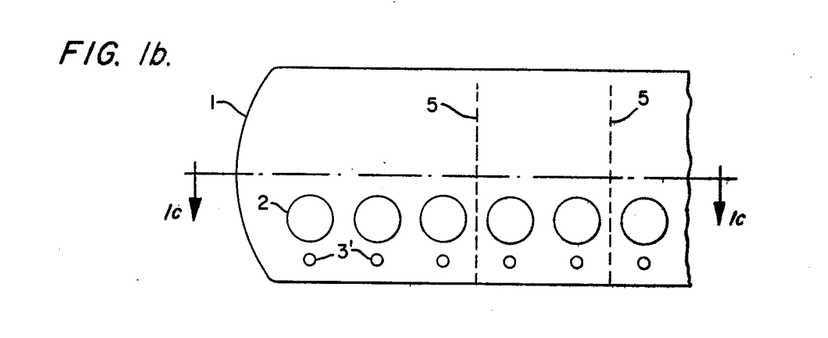
FIG. 1b shows the definition of the term "cross section area" as used in the definition of specific cross section load $L_{spF}$ for the oxidation according to FIGS. 1a, 2, 3 or 4.

In the preferred construction, the separating baffles exhibit a continuously diminished height from one end to the other of the reactor, so that the liquid phase can flow under the effect of gravity from one stage to the next (see FIG. 1a). The liquid phase can also be conveyed from one stage to the next by pumping, as is the case, for example, between the second and third stages in FIGS. 3 and 4.

These two basically different constructions result from various requirements in practice:

(1) In case of a free fall from the reactor inlet to the reactor outlet, the level in the reaction stages provided by the liquid-containing chamber need not be additionally controlled, of course, since the level in each chamber is predetermined by the height of the overflow weirs. The level of the last chamber is maintained constant by means of a conventional level control means.

The height of the overflow weir in the first chamber is determined in such a way that the flow gradient necessary for the respective throughput is produced so that a liquid level remains in the last stage which ensures an economical operation, i.e. no excessive oxygen breakthroughs. In general, it has been found that the liquid level in each chamber should be at least 3 to 4 meters, and the liquid level is not more than about 10 meters.

Figure 3:
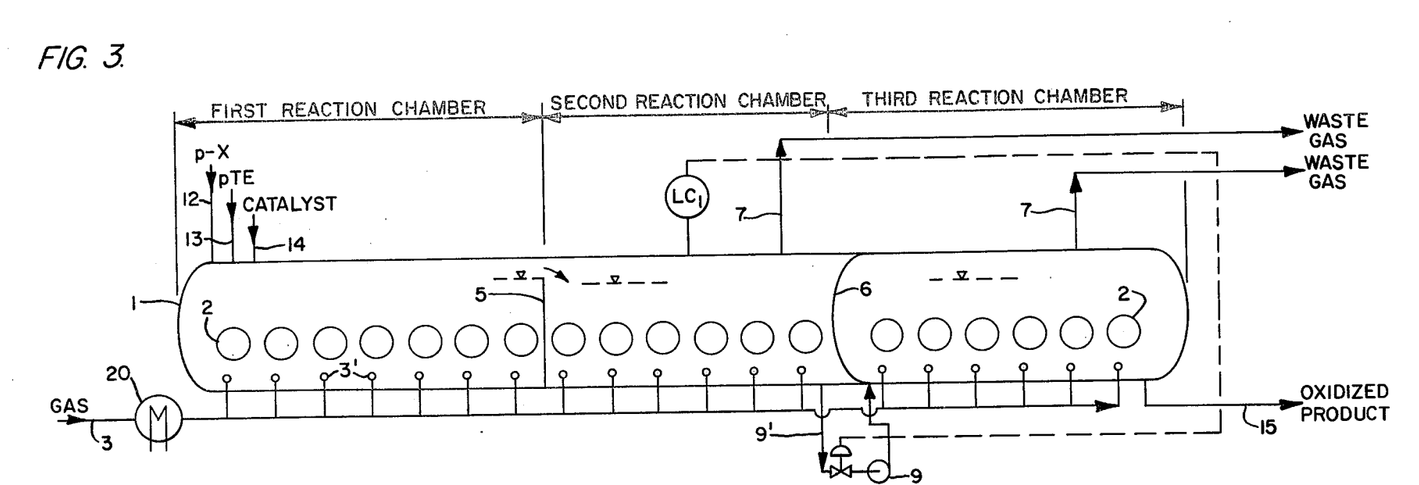
FIGS. 3 and 4 show horizontally disposed oxidation reactors with reaction chambers subdivided by baffles and a plate and with different arrangements for the auxiliary equipment.

In contrast thereto, if it is intended to exploit the volume of the apparatus available in the last reaction stage, i.e. last chamber, to the full extent with a view toward maximally long reaction times, then it is possible to effect pumping from the penultimate into the last stage, as shown in FIG. 3. In case of such an operation, the level in the penultimate stage must, of course, also be controlled, since the liquid in this stage does not flow by gravity to the last stage.

The last-mentioned mode of operation is especially advantageous in practice, since the pT ester oxidation, which takes place predominantly in the last reaction stage, entails a longer reaction time than the preceding p-xylene oxidation, and with a larger volume, i.e. a higher liquid level, higher absolute conversion rates can be attained in the same period of time which, in turn, has economical advantages.

(2) It can be more economical to operate the last stage under such a pressure which makes it possible without auxiliary means to employ the waste gas from this stage once again in another preceding stage, in order to exploit the residual oxygen content. In other words, with a minor additional expenditure, the possibly occurring high residual oxygen content of about 6% can be fully exploited by a minor raising of the pressure. This leads to a reduction in the total amount of air employed and thus to a noticeable economical advantage, if the driving energy for the compressors is correspondingly expensive.

The selected mode of operation generally is dependent on the local prices for the energy to operate the pumps and compressors, as well as on the initial investment costs.

The aromatic reactants need not be introduced into each chamber. It is sufficient if they are fed only into the first chamber. However, if they are also fed to subsequent stages, these chambers can also serve as inlet chambers, for example, in case of repair. Thus, it will be appreciated that the aromatic reactants which remain unreacted in the first stage will pass to the next successive stage or chamber.

Under practical conditions, the introduction of additional p-xylene to the last stages has proven to be advantageous since this increases the oxygen exploitation.

The aromatic reactants can be added at the head, i.e. top, as well as at any other places of each stage of the reactor. Due to the introduction of air, such high turbulences are produced that an almost ideal intermixing of the liquid takes place and thereby the starting aromatic reactants are prevented from overflowing via the separating baffle into the next chamber.

As mentioned above, the individual stages are passed through in succession by the liquid phase reaction medium. This is necessary since each reaction stage has an optimum temperature which should, on the one hand, be so low that the reaction takes place with a particularly low amount of losses, but, on the other hand, is also so high that a sufficient conversion is attained.

These temperatures are set by varying temperatures in the cooling bundles. In the oxidation of p-xylene and methyl p-toluate, which may be present in a weight ratio of from 1:1 to 1:3, the temperature will vary from 80°–250° C. Generally, the temperature of the first stage is maintained at about 150°–155° C. and the temperature in the successive stages is increased by an increment of about 5° C.–10° C. In some cases the temperature for a group of stages is maintained at the same value. For example, the temperature in the first and second stages may be at about 155° C.; in the third and fourth, at about 160° C.; and in the fifth and sixth stages, at 165° C. Advantageously, the reactor construction of this invention provides several successive stages within one reactor unit so that the temperature can be more gradually changed from the first stage to the last stage without a substantial investment cost.

The residence time in each stage is determined by the spacing of the overflow baffles. The quotient from the throughflow quantity and the liquid volume between two baffles yields the provided residence time.

Preferably, the same residence times are utilized for all stages. Depending on the desired production and the chemical yield, the temperatures can be adjusted to be higher and lower. High temperatures mean a high throughput; low temperatures mean a lower throughput, the temperature limits being set by the desired yield. The basic aspect of the invention resides in that with otherwise identical or improved relationships with respect to yield and production, the residence times of the reaction mixture in the reactor can be substantially reduced, for example, to one-third or a quarter of the previously customary values. Shorter residence times simultaneously lessen the probability of undesired secondary reactions. Thus, it is possible to build smaller apparatus, i.e. less volume, which show the same efficiency as the previous, large-size ones, with identical yields.

The heretofore customary residence times in the conventionally tall single stage reactors were not determined by the physicochemical conditions but rather by the geometrical dimensions of the reactors. The geometrical dimensions of the reactors, however, were determined by the type and character of the cooling surfaces. Due to the arrangement of the cooling surfaces according to this invention, it has now become possible to follow the physicochemical conditions much more closely and to conduct the reaction at specific air supply quantities $L_{spA}$ of, for example 1–4 $Ndm^3$ of air per kg. of reaction mixture per minute; or under specific cross section loads $L_{spF}$ of 150–1,000 $Nm^3$ of air per hour per square meter of cross section area, primarily 150–300 $Nm^3/m^2 \cdot h$. In conventional oxidizers, usually only specific air supply quantities of 1–1.7 $Ndm^3/kg \cdot min$ are attained, wherein the specific cross section loads are in the range of 1,000 $Nm^3/m^2 \cdot h$.

Quite specific advantages are obtained precisely from the fact that, inter alia, p-xylene and pT ester are oxidized in the reactors together in the presence of a Co-Mn-containing catalyst.

In laboratory apparatus and small-scale oxidizers with a favorable ratio of their cylindrical surface used for cooling purposes to the volume, space-time yields were attained which could not be realized in technical apparatus, even without considering economy. For this purpose, it would be necessary to have specific cross section loads $L_{spF}$ of more than 1,000 $Nm^3/m^2 \cdot h$. At such large amounts of air, nowadays customary large reactors exhibit an extraordinary amount of foaming. This effect is greatly dependent on the product, which manifests itself in that the foaming tendency increases with an increasing p-xylene concentration in p-xylene/pT ester mixtures. In the oxidizers according to this invention, it is now possible to increase the specific amount of air supplied ($Ndm^3/kg$ reaction mixture·minute) even in case of far lower specific cross section loads ($Nm^3/m^2·h$) to such an extent that it is definitely comparable to the values obtained in laboratory apparatus, and this leads to the heretofore described advantages.

It is furthermore very important that lower specific cross section loads lead to a specifically smaller reaction heat load, since per unit of volume of reactor more liquid is available for heat transport, which, in turn, leads to lower losses in yield. In laboratory tests, it was possible to prove that with otherwise identical relationships, i.e. also at equal specific amounts of air supplied per kg of reaction mixture, the combustion losses increase if certain optima of specific cross section load are exceeded. The desired, low values are entirely intolerable in conventional oxidizers from an economic viewpoint, while they are possible in case of horizontally disposed oxidizers.

In accordance with this invention, the cooling conduits are positioned in a horizontal arrangement at an optimum distance from the oxidizing gas inlet means located at a maximally low level in each of the chambers. The optimum arrangement is obtained in oxidizers according to FIGS. 1a–4 wherein each bundle of cooling conduits is positioned a predetermined distance above the gas inlet means to effect cooling immediately upon initiation of the reaction. In this connection, it is to be considered advantageous that the total cooling surface is at a spacing of preferably 1–2 m from the gas inlet means.

Experiments were used to prove that the primary reaction takes place at this distance from the oxidizing gas inlet, i.e. the greatest amount of heat is likewise produced at this location and must be immediately passed on to the cooling system. In the oxidation systems utilized nowadays, the thus-produced heat of reaction must be transported over relatively long paths to the surfaces of the cooling system, leading to a temporary local overheating of the oxidized product. However, since overheating of the oxidized product can lead to losses in yield, the short cooling paths of the novel construction allow one to expect special advantages. Besides, on the side of the oxidized product, due to turbulence caused by the transversely directed stream to the cooling surfaces, the heat transfer is so satisfactory that it is worthwhile to change over on the coolant side from the nowadays customary natural circulation systems with low heat load and thus lower heat transfer values to forced circulation systems having very good heat transfer values. The heat transfer then becomes so satisfactory that savings in cooling surface can result of 50% as compared with nowadays customary constructions.

Special conduit branches, product-conveying systems, and similar means are possible, but not required, in order to attain the above-described advantageous effects. The product speed around the cooling surfaces of the conduits is dependent practically only on the physical conditions of the rising air and/or of the oxidizing gas. The arrangement of the cooling surfaces in the form of individually exchangeable tube bundles seems particularly advantageous. Within each bundle, each conduit individually has product and reactants flowing therearound, due to the predetermined spacings between the conduits; whereas the temperature-controlled coolant is in each conduit. It will be appreciated that the conduits may have circular, flat-oval, rectangular, and other cross-sectional configurations and are arranged horizontally to extend around the width of the reactor tank. Moreover, control means includes appropriate valves, pipes, flow meters and like accessory equipment are used to control the flow of cooling medium at predetermined temperatures through each bundle of cooling conduits.

The actual liquid volume during the reaction can be adjusted (by varying the height of the overflow baffles and/or the level control) so that the specific amount of air LspA offered does not exceed 0.5 to 4 $Ndm^3$ air/kg reaction mixture·min. Higher values are possible, but burdened according to our experience with high losses in yield by combustion and secondary reactions. Lower values are likewise possible, but uneconomical.

High LspA values are possible normally only in case of low liquid coverage. In this connection, the air used as an oxidizer must be preheated. In case the air is not heated, the danger of oxygen breakthrough exists in case of liquid coverages of about 1 meter or lower. The term "liquid coverage" refers to the height of the liquid level above the oxidizing gas inlet openings in the reactor. In the second and subsequent reaction stages, the danger of oxygen breakthrough at high amounts of air supplied and at low liquid coverages can also be lessened by the use of agitating units.

The different mode of constructing the oxidizers results from the varying numbers of stages and the energy and raw material costs which may have to be considered, and the space available.

The provision of a large number of stages was associated with a greater cost for air inlet structures in conventional constructions than a small number of stages. In the continuous conductance of chemical reactions, however, a high number of stages is always advantageous—except in case of reactions of the 0th order. With an increasing number of stages, the space-time yield approaches the optimum of the discontinuous process, on the one hand, and, on the other hand, a good temperature adaptation will be achieved to the requirements of the progression of the reaction. The latter is especially significant if mixtures such as, for example, the mixture of p-xylene and pT ester, are to be oxidized wherein the individual components have different temperature optima during the oxidation. Besides, the amount of the circulation products in a process using a multi-stage operation is strongly reduced; this amount, as experience has shown, is greatest in case of a single-stage, continuous oxidation.

In a conventional mode of construction, a three-stage structure was especially advantageous in view of the costs for raw materials and energy. In the horizontal arrangement of the novel apparatus of this invention, larger numbers of stages can be realized without any greater expenses by the additional installation of separating baffles which control the liquid level. However, even with a merely three-stage mode of operation and thus a simpler structure, the advantages of the novel system can be realized almost to the full extent. Small numbers of stages will always be used in practice if the apparatus has a small throughput efficiency and thus it becomes more difficult, i.e. more expensive for purely geometrical reasons to introduce several stages.

Basically and generally one can say that it is particularly advantageous for constructional reasons to design the stages with an equally large volume and equally large cooling surfaces. This leads to very simple welding constructions which can be composed in the manner of modules.

Figure 4:
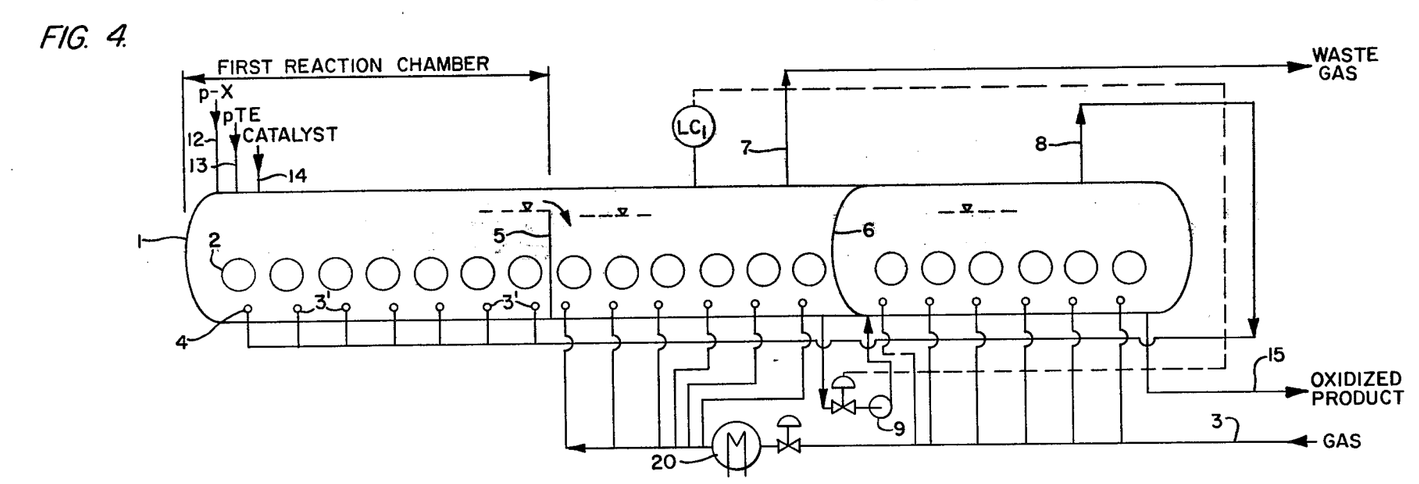

FIGS. 3 and 4 show those reactor constructions which can be used in practice with smaller throughput efficiencies. However, attention should be drawn here above all to the expedient of returning unused oxygen-containing gases, i.e. waste gases, from the last stage to the first stages for exhaustive reaction. In theory, it makes no difference which proportion is returned. It will be especially advantageous to return the entire quantity. It is, by the way, definitely possible to introduce not only waste gas or air, for example, into separate chambers, but also to introduce both materials together into one chamber. In this connection, the limits of foam evolution must, of course, be considered under practical conditions. The already mentioned cross section load limits result. The higher proportion of inert gas connected therewith can be utilized for mixing purposes (for example in appropriately constructed, conventional nozzles) and for use as heat transport agent. The oxygen dilution effect occurring in this mode of operation counteracts, of course, local hot spots in the product. If only waste gas is introduced into the first stage, then it is advantageous, but not necessary, to select the volume of this first stage so that the gas load is at the upper limit of possibility, since only a relatively low amount of reacting oxygen is present in the gas and thus the load of reaction heat is low.

In the vertical reactor design, the aforedescribed advantages can only be realized in part. The main advantages in this design reside in the low requirement of ground area.

Thus, in general, the apparatus of this invention makes it possible, under the same pressure, to increase the specific amount of air supplied $L_{spA}$ per kg of mixture to be oxidized, and to lower the specific area load $L_{spF}$ as well as to intensify the removal of the evolving heat of reaction. These advantages are attained even in large-scale technical plants where values for the amount of air supplied are achieved which heretofore have not been possible due to the physical laws to which a bubble column is subjected and due to a strong foam evolution. These conditions have an especially favorable effect in the mixed oxidation of p-xylene with pT ester under pressure of between 3 and 10 bar and at temperatures of between 130° and 200° C. In case of other non-foaming products and/or in processes which do not produce such intense heat of reaction, such considerations are not as significant. The same holds true for processes which do not remove the heat of reaction via cooling bundles and which realize high amounts of air supplied by operating under comparitively high pressure and by the use of different catalyst systems.

Various embodiments of the invention are briefly hereafter described in the appended claims in connection with the embodiments shown in the accompanying drawings wherein:

FIG. 7 shows a vertically disposed oxidation reactor with superimposed chambers subdivided by plates, wherein external conduits are extensively dispensed with.

Figure 1C:
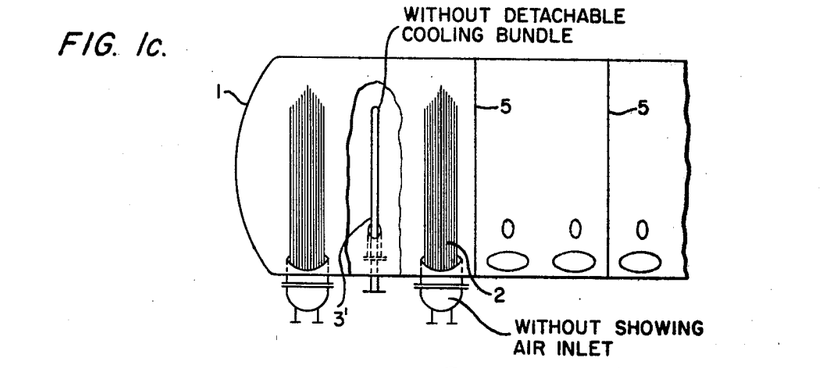
FIG. 1c shows the view of the oxidizer of FIG. 1b across the plane A—A.
Figure 1D:
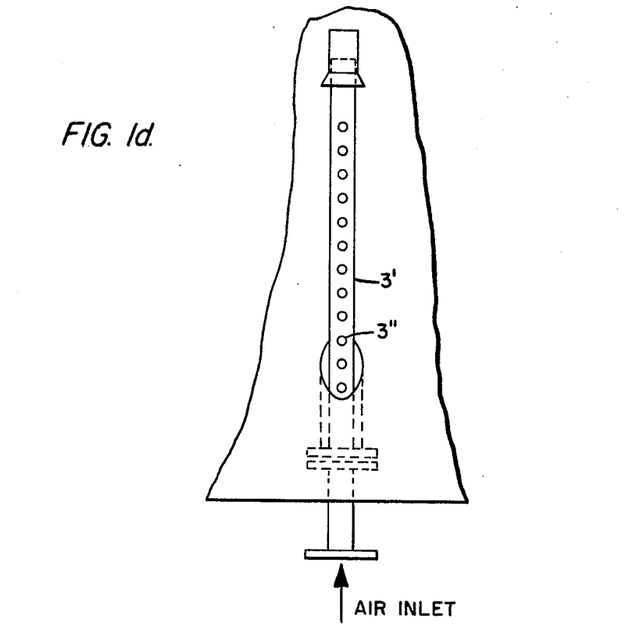
FIG. 1d shows details of the oxidation air inlet for the oxidizer according to FIG. 1b.
Figure 2:
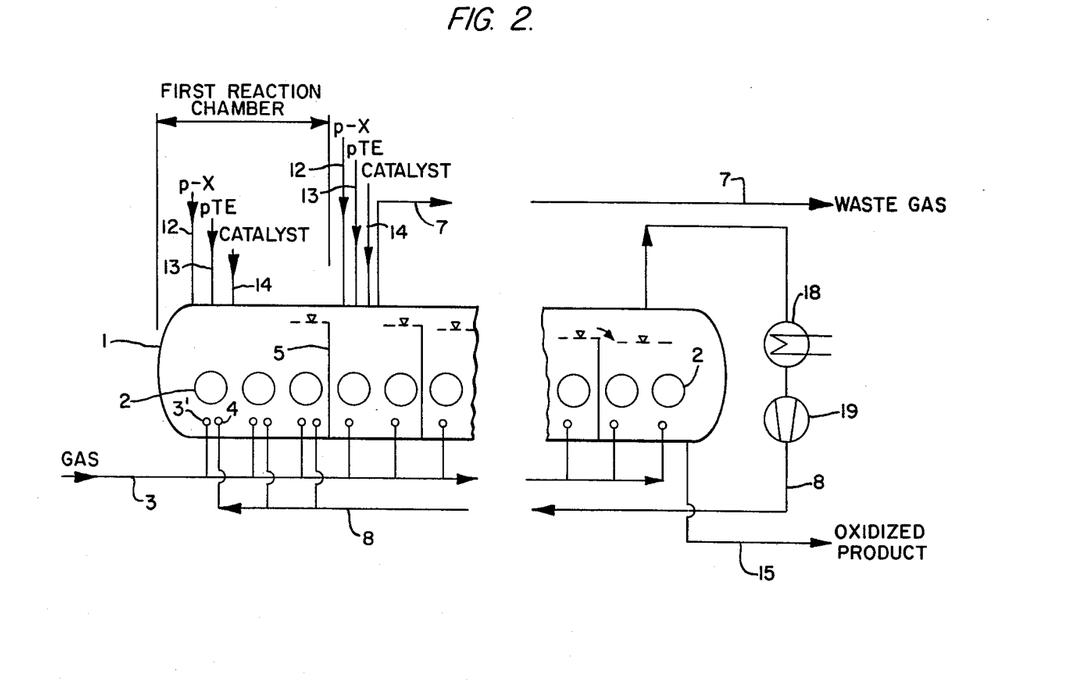

Referring to the drawings in greater detail, FIGS. 1a and 2 each illustrate an oxidation reactor in the form of a horizontally disposed, cylindrical tank 1 made-up of several side-by-side reaction chambers separated from one another by bulkheads or walls 5, with horizontally arranged cooling pipe systems 2, an oxidizing gas feed system 3, including individual gas inlet devices 3', a discharge outlet means for the oxidized product designated by 15, circulating pumps 10, and agitator units 11. Entirely or partially reacted oxidizing gas, e.g. air, is discharged via the vapor conduits 7 and/or is recycled via recycling conduits 8 as well as the compressor 19, as shown in FIG. 2, at 4 into the initial reaction chambers. The inlets 12, 13 and 14 serve for the feeding of p-X, pTE, and catalyst, e.g. a cobalt or manganese compound or mixture thereof in solution or slurry form. The heat exchanger 20 serves for preheating the oxidizing gas, e.g. air; heat exchanger 18 serves for cooling the recycled gas. As shown in FIGS. 1c and 1d, the gas inlet devices 3' each comprise a pipe or conduit 3' that has a plurality of spaced nozzles or orifices 3" and that extends across the bottom portion of the reactor. The gas inlet devices 3' are distributed over the longitudinal section of each chamber to insure uniform distribution of the oxidizing gas, e.g. air throughout the reaction mixture in each chamber.

The agitating unit shown in FIG. 1a is provided only if the additional expenses caused by its installation and operation are covered by the saving in oxidizing air. Typical values for the residual oxygen content without agitating unit are 3–4% $O_2$, with agitating unit 1–2% $O_2$ in the waste gas. Such agitating units are preferably used in the stages wherein the reactivity is at such a low level that the residual oxygen content justifies the use of such units, i.e. preferably in the second and subsequent stages.

FIGS. 3 and 4 show other horizontally disposed oxidation reactors 1 with reaction chambers subdivided by bulkheads 5 and a plate 6, the third stage or chamber is maintained at a higher pressure than the first and second stages by complete separation with plate 6 and by pressure control valves in the vapor conduits 7 and 8. The pressure differences are bridged by the pump 9 via conduit 9' for the reaction mixture. The remaining reference numerals have the same significance as in FIGS. 1a and 2. In the reaction chambers subdivided by the plate 6, such a pressure is maintained that oxidizing gas which has not as yet been completely reacted can be returned via the recycling conduits 8 without a blower into the initial reaction chambers. In these figures LC designates a liquid control means for controlling the liquid level in the second stage and for regulating the flow of liquid reaction medium for this stage to the next. The liquid level in the third stage is regulated by similar control means (not shown) which regulates the flow of liquid through outlet 15.

Figure 5:
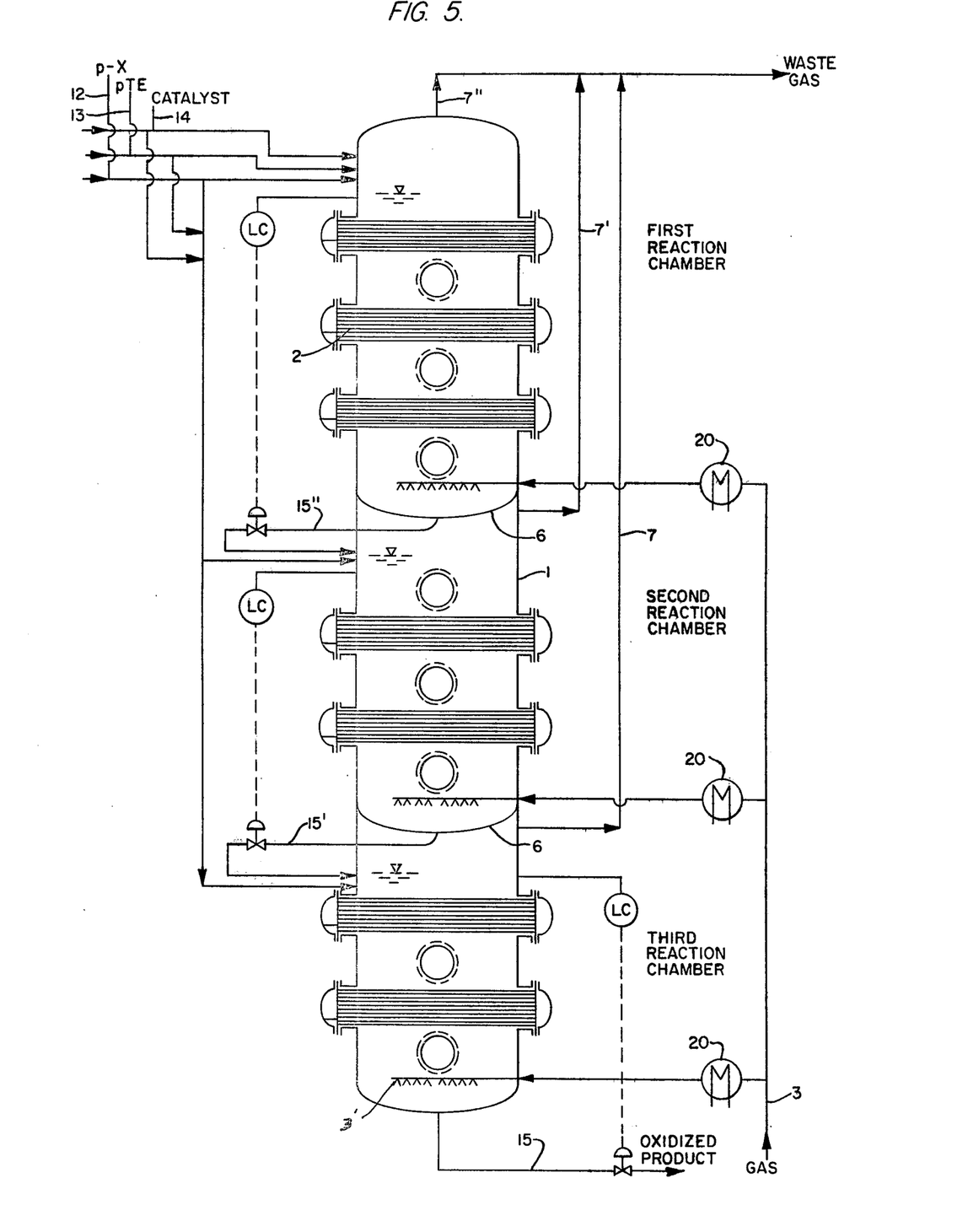
FIGS. 5 and 6 show vertically disposed oxidation reactors with superimposed chambers subdivided by plates and with different arrangements for auxiliary equipment.
Figure 6:
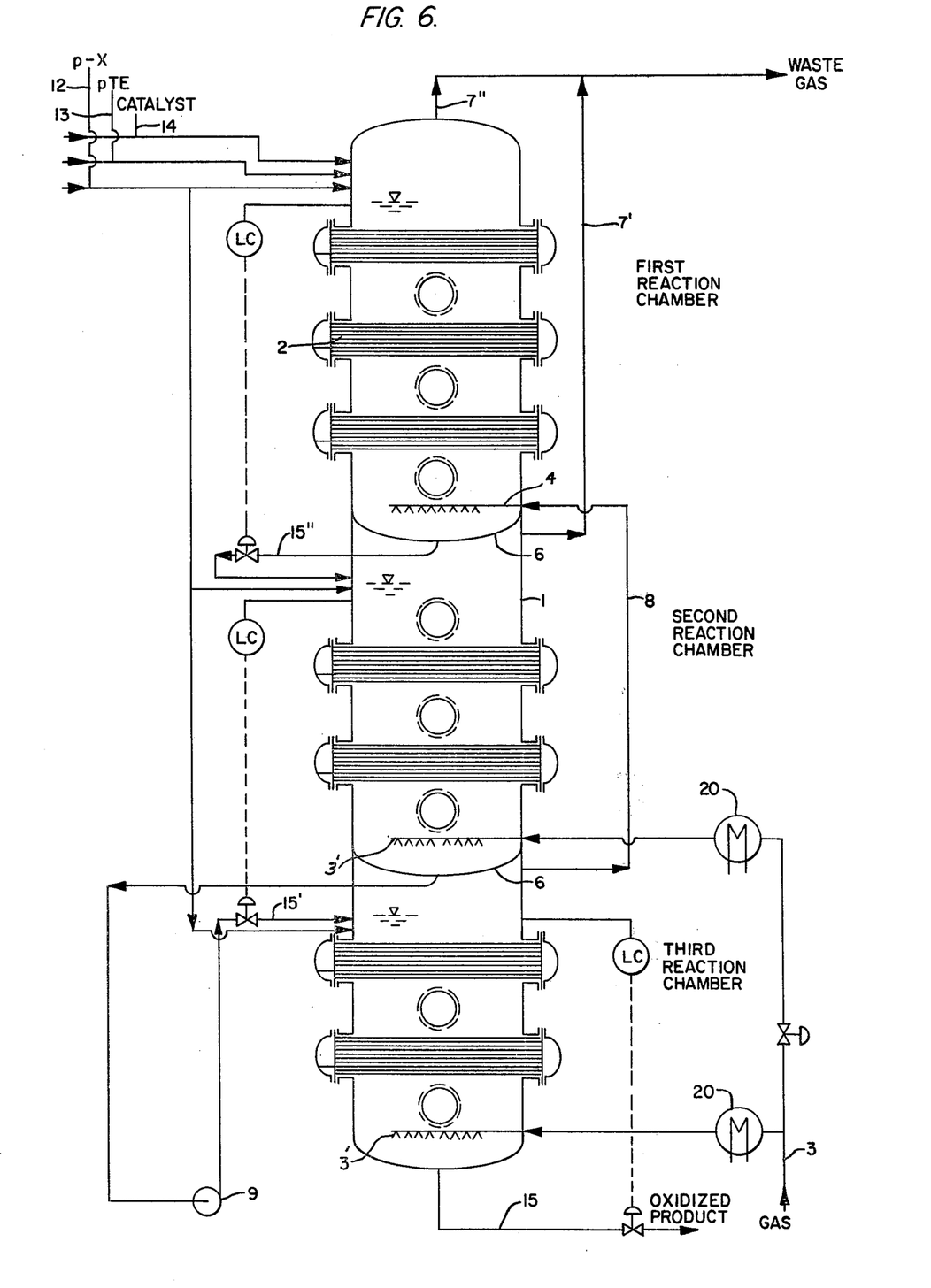

According to the illustration of FIGS. 5 and 6, the reaction chambers in the oxidation reactors 1 are arranged in superimposed relationship and separated by plates 6; these chambers comprise cooling pipe systems 2, oxidizing gas feed systems 3, 4, and discharge conduits 15, 15' and 15'' for the reaction mixture of each stage. In FIG. 5, the reactor waste gas is removed from each stage via conduits 7, 7' and 7''. Via the vapor conduits 8, in the reactor of FIG. 6, partially reacted oxidizing gas is conducted from the lower reaction chamber into the upper reaction chamber. In case of varying pressures, the pump liquid 9 is employed to pump reaction mixture from an upper reaction chamber into a reaction chamber disposed therebelow because this reaction mixture cannot flow by gravity from the upper to the lower chambers due to the higher ambient pressures in the lower chambers, which chamber pressure makes it possible, to effect the passage of the waste gases from a lower chamber to an upper chamber. The remaining reference numerals refer to like elements as shown in FIGS. 1a and 2.

Figure 7:
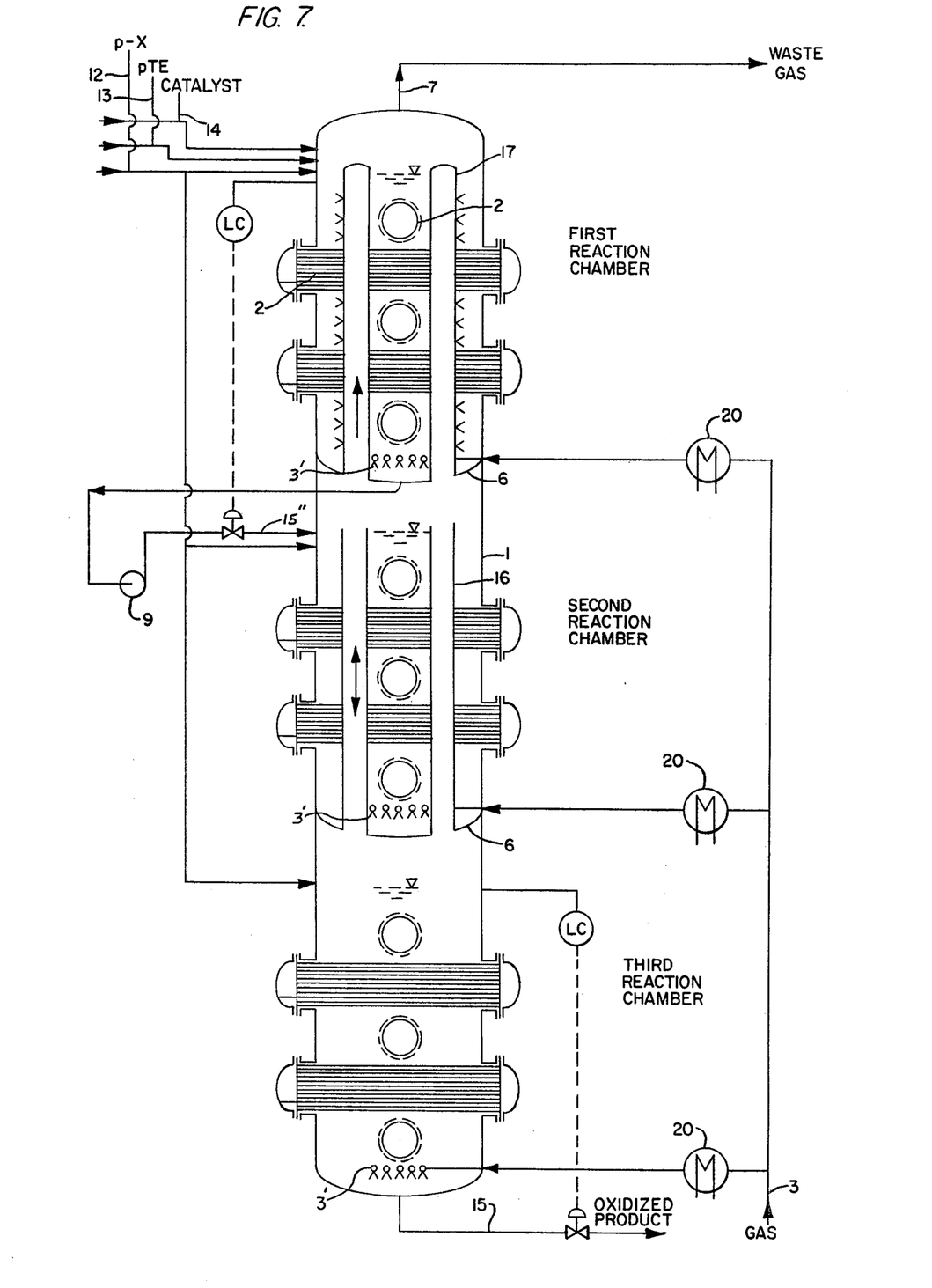

According to the illustration of FIG. 7, the reaction waste gases are conducted from one reaction chamber into the other one through flues 16 of such a size that the liquids can flow countercurrently into the subsequent reaction chamber. In the top reaction chamber, the flues 17 are fashioned to be sealed at the top. In this case, the flues of the top chamber are provided with lateral openings or bores to permit passage of the oxidizing gas into the liquid phase medium.

It is just as well possible for the flues in the top reaction chamber to remain open. In this case, the pump 9 is not required. The remaining reference numerals indicated in FIG. 7 have the same significance as in FIGS. 1a and 2-6.

In case of identical pressure in all chambers, a compressor 19 and optionally an intermediate cooling unit 18 are provided in the recycling conduits 8, as illustrated in FIG. 2.

For the oxidizing gas feed system 3 and the recycling gas inlet 4, the area available in the horizontally disposed cylindrical oxidation reactor according to FIGS. 1a, 2, 3 and 4 is considerably larger than in case of the vertically set-up arrangement according to FIGS. 5, 6, and 7. A still further increase of the air feed cross-section can be obtained in the horizontally located embodiment by enlarging the length of the reactor.

The height of the liquid level attainable in the horizontal reactor is predetermined by the diameter (and the height of wall 5); whereas in case of the upright reactor a certain height can be set in each stage. Also, in the horizontal reactor any desired combinations of recycling means for the reaction mixture and oxidizing gas are possible. If the transport of the reactants from one reaction chamber into a neighboring reaction chamber is effected by means of pumps 9, then valves with a liquid level control are connected in series with the pumps, as indicated in FIGS. 3, 4, 6, and 7.

The residence time of the reactants which are present and/or suspended in the liquid phase is adjusted in the individual reaction chambers by level control units, as indicated in FIGS. 3, 4, 5, 6, and 7, which units are designated by LC.

In the cooling pipe systems 2, evaporative cooling is normally possible with natural circulation, as long as the surface temperatures are maintained so that reaction product cannot be crystallized. Economical calculations are govering when deciding whether natural circulation or forced circulation is selected in the case of condensate evaportion. Liquid or gas circulation cooling units without evaporation are less favorable from an energy viewpoint due to the dual occurrence of a heat transfer resistance. It is likewise possible to employ liquid circulation systems wherein the liquid, heated under pressure, is vaporized in a flash chamber.

Figure 8A:
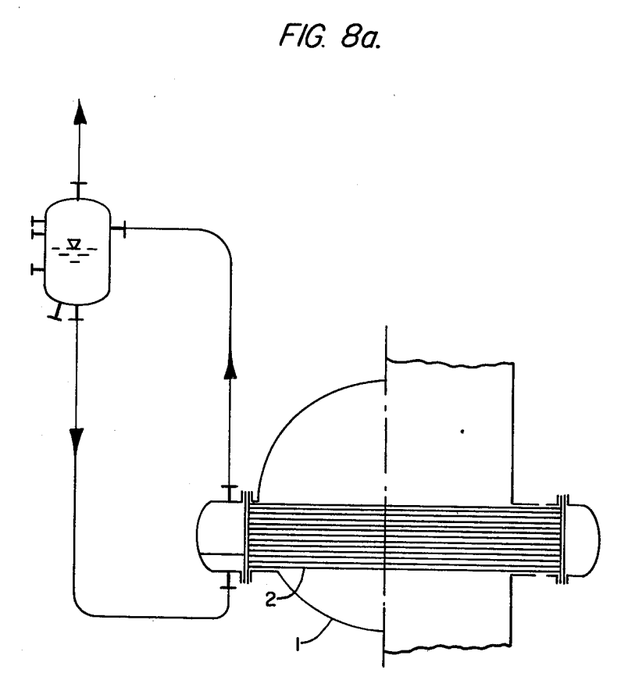
FIGS. 8a, 8b and 8c show details of a cooling pipe system with a coolant cycle.

A typical installation with natural circulation is illustrated in FIG. 8a.

Figure 8B:
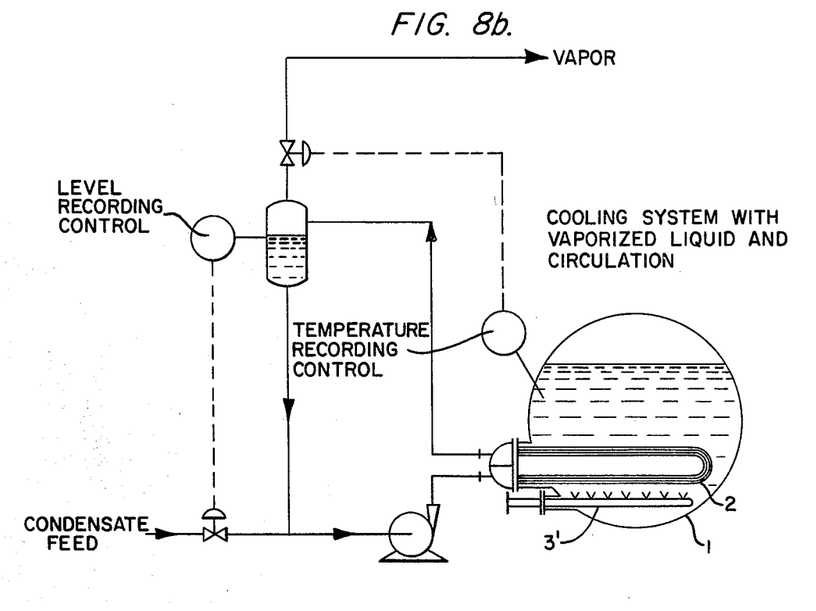

In FIG. 8b a cooling system with evaporation of condensate and forced circulation is illustrated.

Figure 8C:
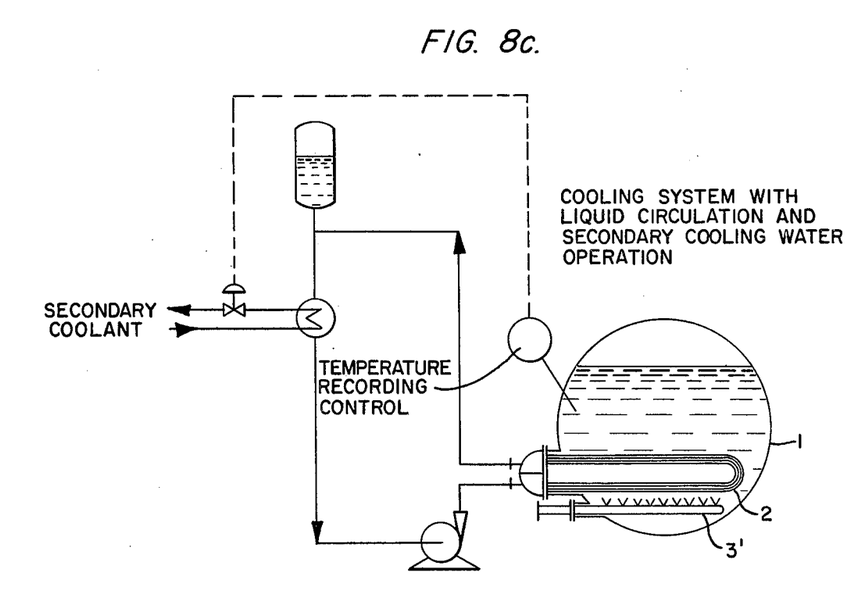

In FIG. 8c a cooling system with secondary cooling of the liquid by a coolant and forced circulation is illustrated.

As compared to the state of the art, the invention achieves the advantages set out hereinbelow:

The required reaction chambers are substantially smaller; the area and three-dimensional space occupied by the construction of this invention amounts to about 20-50% of the heretofore necessary values. For the previous constructions, overlong cooling pipes (e.g. 18 meters) had to be utilized. The lengths for the cooling pipes in the oxidation reactor of this invention range at about 5-6 meters. The large vapor chambers are eliminated; the welding seams thus can be more readily controlled and are better accessible. A pipe rupture in the previous constructions, in contrast thereto, resulted in a considerable production loss, if an entire oxidation reactor must be shut down for repairs.

As compared to the previous constructions, a large number of cooling conduits, combined into cooling conduit systems 2, is installed in the structure of this invention, so that the failure of one cooling conduit system can hardly lead to a loss in production. The defective cooling pipe system can be sealed off by a slide valve and repaired at a most favorable point in time. Due to the smaller diameters of the oxidation reactors of this invention, transportation problems will no longer occur to the previous, excessive extend on the way to the installation site.

Due to the more favorable arrangement of the cooling pipe systems exposed to a transverse flow of the oxidizing gas and the reactants, the required cooling surfaces are reduced by 20-50% or thereabove. The saving obtained depends on the type of cooling selected. In natural circulation systems with a normal heat transfer resistance, the saving in cooling surfaces is at lower values within the framework of the aforementioned range.

The following Table I shows a comparison of the cooling surfaces and oxidation reactor volumes as well as the air flow cross-sections, required at an identical throughput and identical heat flow, for the conventional type of construction and for the structure according to this invention in the horizontal position.

The values of Table I apply to the oxidation in a three-stage operation with a production schedule of about 140,000 tons per year of dimethyl terephthalate (DMT) by the air oxidation of mixtures of p-X and pTE in the liquid phase in the presence of heavy-metal-containing oxidation catalysts under elevated pressure and at an elevated temperature, obtaining a reaction product containing primarily mixtures consisting of p-toluic acid and monomethyl terephthalate, and by the subsequent esterification with methanol and separation of the thus-produced ester mixture.

The main reactions are:
Oxidation:

$$CH_3—C_6H_4—CH_3 + 3/2O_2 \rightarrow CH_3—C_6H_4—COOH + H_2O$$

$$CH_3OOC—C_6H_4—CH_3 + 3/2O_2 \rightarrow CH_3OOC—C_6H_4—COOH + H_2O$$

Esterification:

$$CH_3—C_6H_4—COOH + CH_3OH \rightarrow CH_3—C_6H_4—COOCH_3 + H_2O$$

$$CH_3OOC—C_6H_4—COOH + CH_3OH \rightarrow CH_3OOC—C_6H_4—COOCH_3 + H_2O$$

TABLE I

| | Conventional Construction Oxidation Reactor | | | Horizontal Construction with Pipes Exposed to Transverse Flow Stage | | |
|---|---|---|---|---|---|---|
| Number | 1 | 2 | 3 | 1 | 2 | 3 |
| Cooling Surfaces (m²) | 2600 | 2300 | 1900 | 1400 | 1200 | 1200 |
| Volume (m³) | 399 | 404 | 410.5 | 138 | 113 | 120 |
| Air Flow Cross Section (m²) | 19 | 18 | 18 | 25.9 | 21.6 | 22.2 |

The term "conventional construction" in Table I denotes the separate arrangement of three series-connected oxidation reactors of the type shown in U.S. Pat. No. 3,065,061.

The term "horizontal construction" in Table I denotes the apparatus of this invention, for example, as shown in FIGS. 1a, 2, 3, and 4 of the drawings, and in particular that of FIG. 3.

The data of Table I reveal that the apparatus of this invention requires, in the form of horizontal construction with pipes exposed to transverse flow, merely about 56% of the cooling surface (in m²) of an arrangement in the conventional mode of construction with three series-connected oxidation reactors.

The required oxidation reactor volume (in m²) amounts, in the device of this invention according to Table I, only to about 30% of the volume required in case of a conventional construction of the oxidation reactors.

The air flow cross-sections (in m²) in the device of this invention are, according to Table I, considerably larger than in devices of a conventional type of structure.

Consequently, the initial investment costs are markedly lower for the apparatus of this invention with increased output, as compared with an arrangement according to the prior art. Extensive savings are also obtained by the elimination of connecting pipelines, measuring and control units, safety devices, and lower building costs as compared with the three-stage design with three series-connected individual oxidation reactors.

A larger number of reaction stages can be realized with the oxidation reactors of this invention without considerable expenses. By the optimum conductance of the process and a more uniform residence time, a higher selectivity of the process is attained, leading to savings in energy and higher yields.

The spatial distance between the site of introducing the oxidizing gas, denoted by 3' or 4, and the cooling surfaces 2 is reduced, especially in case of the horizontal reactor, to a fraction of the previously customary values. Only short paths are encountered for removing the heat of reaction, making it possible, together with the smaller volume of the oxidation reactors of this invention, to provide a more gentle handling of the product, a higher chemical yield, and a higher space-time yield. The installation of agitator units 11 to improve the distribution of the air and/or of the oxidizing gas, and the provision of circulating pumps 10 for a more intimate intermixing of the reactants becomes technically feasible, for example, also in the upper chambers of the upright oxidation reactors according to FIGS. 5, 6, and 7. This leads to higher throughputs, more uniform residence times, and an improved oxygen utilization.

When recycling already reacted and cooled vapors into other reaction chambers, the results are a more intensive bubble layer, an increase in the cooling effect, an improved distribution of the oxygen, as well as a lowering of the oxygen concentration.

By circulating the reaction gases, it becomes possible to operate with variable oxygen concentrations and/or the turbulence can be enhanced, leading to higher throughputs and optimizing the oxidation conditions.

The likewise possible preheating of the oxidizing gas increases the reaction velocity.

The compression costs can be reduced by the proportion corresponding to the eliminated length of the liquid column.

The heretofore customary residual oxygen contents of 4% in the last stage can be fully exploited in the oxidation reactors of this invention, especially in case of the upright construction according to FIGS. 6 and 7.

FIGS. 1a, 1b, 1c, 1d, 2–8a, 8b and 8c of the appended drawings represent preferred embodiments of the invention. It is readily possible for those skilled in the art to derive other advantageous embodiments from the present description, above and beyond those shown in the drawings.

The following example relates to the oxidation of a mixture of p-X and pTE in the apparatus of this invention, i.e. of the type shown in FIG. 4 wherein the last stage is maintained at a higher pressure.

EXAMPLE

The continuous oxidation of a mixture of 16,208 kg/h of p-X and 23,878 kg/h pTE is conducted in a horizontally disposed reactor made of a high-grade steel comprising 3 adjacent reaction chambers successively traversed by the reaction mixture, with bundles of horizontally installed cooling pipes as the cooling pipe system, oxidizing gas feed systems in all reaction chambers, as well as inlets, vapor conduits, and a discharge system for the oxidized product in part of the reaction chambers, this reactor having a volume of 370 m³ and a cooling surface of 3,800 m²; this continuous oxidation is carried out while supplying 122 kg/h of aqueous catalyst solution of the acetates of cobalt and manganese containing 30 g/l $Co^{2+}$, and 2.4 g/l $Mn^{2+}$ as well as 51,584 kg/h of air at a temperature of about 155°–165° C. and under a pressure of about 7 bar, thus obtaining 38,382 kg/h oxidized product and 53,350 kg/h of waste gas.

The oxidized product has the following composition:
- 2–5 weight percent of higher-boiling components (HB)
- 12–18 weight percent of terephthalic acid (TPA)
- 20–28 weight percent of monomethyl terephthalate (MMT)
- 10–15 weight percent of dimethyl terephthalate, dimethyl isophthalate, dimethyl orthophthalate (DMT, DMI, DMO)
- 17–23 weight percent of p-toluic acid (pTA)
- 16–22 weight percent of methyl p-toluate (pTE)
- 3–6 weight percent of benzoic acid methyl ester (BME)
- 1–2 weight percent of p-xylene (p-X)
- remainder, weight percent of low-boiling components.

It will be appreciated from the heretofore described description that this invention also contemplates a unique process for effecting the oxidiation of alkyl aromatics, wherein the oxidation is effected in the multi-stage reactor.

Moreover, it will also be recognized that the preferred form of the reactor tank is a cylindrical unit wherein the length is sufficient to provide at least three stages and the diameter large enough to ensure that the cross-section of the liquid phase in each stage, i.e. chamber, will be sufficient to provide a specific cross-section load of from 150 to 1,000 Nm³/m².h for the reactor with a minimum liquid coverage of from 1 to 2 meters. The cross-sectional configuration of the reactor tank may be semi-circular, rectangular, oval, triangular, etc. The circular cylindrical tank is the preferred construction.

It will be appreciated that normally cooling is effected with evaporating condensate with the cooling pipe systems. With this type of cooling, temperature differences occur only on the coolant side, but these can be neglected, since the vapor pressure is identical over the entire area. An almost ideal temperature compensation is provided in the reaction mixture due to the turbulence connected with the large amount of oxidizing gas introduced. The temperature differences arising in the circulation of cooling medium in the cooling pipes are controlled to be on the order of about 5°–10° C. and thus have an insignificant effect on the reaction conditions for purposes of this process.

The height of the liquid level in the individual chambers is dependent on the specific air supply with the specific cross-section load being a basic control parameter.

The term "cross-section area" as used herein means, in a horizontal reactor, the entire surface of the reactor in the center of the vessel above the cooling pipes, produced by the product of diameter times length.

To prevent the parallel surface in the plane of the air feed pipes from being too small as compared to the cross section area of the reactor the air inlet pipes 3″ should be arranged at a level no lower than about 0.5 meter over the bottom of the reactor.

In case of a vertical reactor, "cross-section area" means the section at right angles to the longitudinal axis of the vessel.

It will be understood that it has been found that in the oxidation of mixtures of p-xylene and pTE a reactor zone having a height of at least 1 to 3 meters is necessary for exploiting the oxygen content of the gas. The reaction zone is that zone extending from the oxidizing gas inlet to the liquid level in the reaction chamber. In general, the oxygen is practically completely consumed by the oxidation reaction at a reaction zone having a height of about 3 meters within the liquid phase reaction mixture. Generally, the height of the reaction zone, determined primarily by the liquid level, is selected to ensure that the oxygen content of the oxidizing gas leaving the liquid phase is, as heretofore described, on the order of from 1 to 4% by volume. Accordingly, level of the liquid reaction mixture need not be greater than about 5–6 meters. Consequently, the total diameter of the horizontal cylindrical reactor of the invention should be at least 2 meters since there must still be a height of about 1 meter above the liquid surface to effect removal of the reacted gas from the reactor.

Advantageously, due to the arrangement of the cooling pipes and the air inlet means, as well as the low liquid levels of the reaction mixture, the horizontal reactor of this invention provides for a reduction in reactor volume, i.e. to about 20–25% of a conventional vertical reactor, for a faster discharge of the waste gases, and for a reduction in the cooling surface required.

What is claimed is:

1. A multi-stage reactor for the oxidation of alkyl aromatics, especially mixtures of p-xylene and methyl p-toluate in a liquid phase reaction mixture with oxygen-containing gases under elevated pressure and at an elevated temperature in the presence of an oxidation catalyst, which comprises an elongated closed tank having a multiplicity of reaction chambers arranged successively from one end to the other end of the tank for containing the liquid reaction mixture at predetermined levels in each chamber, an oxidizing gas feed system for introducing an oxygen-containing gas into each chamber, feed means for introducing at least one alkyl aromatic reactant and an oxidation catalyst into at least one of the chambers, a vapor-collecting conduit means in communication with each of said chambers for removing reaction gas from each of said chambers, discharge means for removing the oxidized product from the reactor tank, and an internally disposed cooling conduit system containing a coolant for removing the heat of reaction from said reactor tank including a group of cooling conduits for each of said reaction chambers, said groups comprising horizontally disposed cooling conduits arranged below the level of the liquid reaction mixture and exposed to transverse flow of the oxygen-containing gas through each of the reaction chambers.

2. A reactor according to claim 1, wherein the reaction chambers are connected to one another so that the liquid reaction mixture passes due to the action of gravity from the first reaction chamber into the subsequent successive reaction chambers.

3. A reactor according to one of claims 1 and 2, characterized in that circulating pump means are arranged to receive liquid in the individual reaction chambers to promote circulating of the liquid therein.

4. A reactor according to claim 2, wherein the horizontally disposed cooling conduits are arranged below the level of the liquid reaction mixture transversely to the flow of liquid reaction mixture from the first reaction chamber into the subsequent successive reaction chambers.

5. A reactor according to claim 1, wherein the reaction chambers are provided with pumps for the removal of the reaction mixture, these pumps being controlled by level control means operatively associated with the chambers from which the reaction mixture is removed.

6. A reactor according to claim 1, characterized in that the reaction chambers are equipped with agitator units fashioned as gas distributing stirrers.

7. A reactor according to claim 1, further comprising a heat exchanger for preheating the oxygen-containing gas to 50°–200° C. before introduction into the reaction chambers.

8. A reactor according to claim 1; wherein said oxidizing gas feed system includes at least one gas compressor, at least one recycling conduit, and at least one gas recycle feed system for the introduction of oxygen-containing vapors resulting from at least one of the final reaction chambers with a lower reactivity of the reaction mixture into reaction chambers having higher reactivities, after the separation of condensible components and said vapor collecting conduit means including at least one conduit for supplying said oxygen-containing vapors to said recycling conduit and another conduit for removing the other vapors collected from the remaining chambers from said reactor to a waste gas treatment unit.

9. A reactor according to claim 8, wherein the final reaction chambers are arranged downstream of the flow of reactant and are those chambers in which the reactivities of the oxidizing reaction provide oxygen-containing vapors with an oxygen content of from 2 to 6% by volume.

10. A reactor according to claim 1, wherein said oxidizing gas feed system includes means for distributing the oxygen-containing gas into a lower portion of each of said reaction chambers below the predetermined level of liquid reaction mixture therein.

11. A reactor according to claim 10, wherein the internally disposed cooling conduit system includes at least one group of cooling conduits in each of said reaction chambers which is disposed immediately above the means for distributing the oxygen-containing gas into said chamber.

12. A reactor according to claim 1, further comprising liquid level control means for maintaining the predetermined level of liquid reaction mixture in each of the reaction chambers at least 1 to 3 meters above the point at which the oxygen-containing gas is introduced into the reaction chamber.

13. A reactor according to claim 1, further comprising liquid level control means for maintaining the predetermined liquid level in each of said chambers at a level that is sufficient to insure reaction down to maximum 6% by volume of oxygen within said oxygen-containing gas passing out of the liquid reaction mixture.

14. A reactor according to claim 1, wherein the feed means are arranged to introduce the at least one alkyl aromatic reactant and the oxidation catalyst into a plurality of reaction chambers.

15. A reactor according to claim 1, wherein the feed means are arranged to introduce the at least one alkyl aromatic reactant and the oxidation catalyst into each reaction chamber.

16. A reactor according to claim 1, wherein the feed means are arranged to introduce the at least one alkyl aromatic reactant and the oxidation catalyst into the first chamber located at one end of the reactor.

17. A reactor according to claim 1, wherein the feed means include conduit means for introducing paraxylene, methyl p-toluate and the oxidation catalyst separately into at least one of said reaction chambers.

18. A reactor according to claim 1, wherein the oxidizing gas feed system is arranged to introduce the oxygen-containing gas into the bottom portion of the reaction chambers below the level of the liquid reaction mixture whereby the oxygen-containing gas is dispersed as bubbles that flow upwardly transverse to the horizontally disposed cooling conduits.

19. A multi-stage reactor for effecting the oxidation of alkyl aromatics in a liquid phase reaction mixture with oxygen-containing gases under elevated pressure and at elevated temperature in the presence of an oxidation catalyst which comprises an elongated tank having a plurality of successively-arranged liquid-containing chambers within said tank, means for feeding at least one alkyl aromatic reactant into at least the first chamber of the successively-arranged chambers, means for feeding an oxidation catalyst into at least the first chamber of the successively arranged chambers, oxidizing gas feed means for introducing a molecular oxygen-containing gas into each of said chambers below the liquid level therein, horizontally disposed cooling conduit means for removing the heat of reaction from said liquid phase reaction mixture, said cooling conduit means being arranged below the liquid phase reaction mixture within each of the liquid-containing chambers so that the oxygen-containing gas introduced into the chamber passes over the cooling means in a direction transverse to the direction of coolant in said cooling means, before exiting from the liquid phase, liquid-level control means for maintaining the liquid level in each of said chambers at a predetermined level, and discharge means for removing the reaction products from the reactor.

20. A reactor according to claim 19, wherein said tank comprises a horizontally disposed cylindrical tank subdivided by vertical separating baffles to define side-by-side reaction chambers and a common vapor space in the tank above the reaction chambers.

21. A reactor according to claim 19, wherein said tank comprises a horizontally disposed cylindrical tank subdivided in part by at least one vertical separating baffle that closes off the tank to define at least one reaction chamber that is separated completely from the other reaction chambers.

22. A reactor according to claim 19, wherein said tank comprises a vertically disposed cylindrical tank having superimposed reaction chambers subdivided by means of separating baffles that close-off the chambers from each other.

23. A reactor according to claim 22, wherein said vapor collecting conduit means includes externally located vapor conduits placing the reaction chambers in communication with one another.

24. A reactor according to claim 22, further comprising vertical gas flues which are open at the top and define the height of the liquid level of the reaction mixture in the associated reaction chamber.

25. A reactor according to claim 23, wherein the upper reaction chamber provides the first stage of the oxidizing reaction and said upper reaction chamber is provided with at least one flue that is vertical, closed at the top and provided with lateral bores defining discharge openings for introducing oxygen-containing gas into said chamber.

26. A reactor according to claim 19, wherein the liquid-level control means includes a discharge means responsive to a liquid-level controller for discharging liquid from the reaction chamber.

27. A reactor according to claim 19, wherein the volume of each of the reaction chambers is selected so that the total capacity of the reactor is from 10 to 1500 cubic meters, that the horizontal cross section area of liquid reaction mixture through the symmetry axis of the reactor in each of the chambers provides cross section loads based on the introduction of air as an oxidizing gas of from 150 to 1000 $Nm^3$ of air per hour per square meter of cross section area at a rate of from 1 to 4 $Ndm^3$ of air per kg of reaction mixture per minute.

* * * * *